US005585634A

United States Patent [19]
Stevenson et al.

[11] Patent Number: 5,585,634
[45] Date of Patent: Dec. 17, 1996

[54] ATTENUATED TOTAL REFLECTANCE SENSING

[75] Inventors: William A. Stevenson, Concord; Mark A. Druy, Arlington; Paul J. Glatkowski, Littleton; Roy A. Bolduc, Amesbury, all of Mass.; Hagai Zmora, Rehovot, Israel

[73] Assignee: Foster-Miller, Inc., Waltham, Mass.

[21] Appl. No.: 315,288

[22] Filed: Sep. 29, 1994

[51] Int. Cl.[6] .................................................. G01N 21/35
[52] U.S. Cl. .................................. 250/339.11; 250/341.2; 250/341.8; 385/12; 385/123
[58] Field of Search .................. 385/123, 12; 250/341.8, 250/339.11, 341.2; 356/133

[56] References Cited

U.S. PATENT DOCUMENTS

| Re. 33,789 | 1/1992 | Stevenson | 250/227.23 |
|---|---|---|---|
| 4,403,826 | 9/1983 | Presby | 250/372 |
| 4,447,546 | 5/1984 | Hirschfeld | 250/365 |
| 4,451,116 | 5/1984 | Pinnow . | |
| 4,595,833 | 6/1986 | Sting | 250/353 |
| 4,671,938 | 6/1987 | Cook | 356/445 |
| 4,788,436 | 11/1988 | Koechner | 250/485.1 |
| 4,798,954 | 1/1989 | Stevenson . | |
| 4,827,121 | 5/1989 | Vidrine, Jr. et al. . | |
| 4,852,967 | 8/1989 | Cook . | |
| 4,893,894 | 1/1990 | Caimi . | |
| 4,981,338 | 1/1991 | Bobb . | |
| 4,988,863 | 1/1991 | Bobb | 250/227.25 |
| 5,000,901 | 3/1991 | Iyer . | |
| 5,044,723 | 9/1991 | MacDonald . | |
| 5,070,243 | 12/1991 | Bornstein | 250/227.23 |
| 5,239,176 | 8/1993 | Stevenson | 250/227.25 |
| 5,436,454 | 7/1995 | Bornstein et al. | 250/339.11 |

FOREIGN PATENT DOCUMENTS

| 417700A2 | 9/1990 | European Pat. Off. . | |
|---|---|---|---|
| 3425715 | 1/1986 | Germany | 356/133 |
| 0253446 | 11/1986 | Japan . | |
| 2047531 | 3/1987 | Japan . | |
| 2236145 | 9/1990 | Japan . | |

OTHER PUBLICATIONS

Compton et al., *In Situ FT-IR Analysis of a Composite Curing Reaction Using a Mid-Infrared Transmitting Optical Fiber*, Applied Spectroscopy, vol. 42, No. 6, pp. 972-979 (1988).

Druy et al., *Fourier Transform Infrared (FTIR) Fiber Optic Monitoring of Composite During Cure, Fiber Optic Smart Structures and Skins II*, SPIE, vol. 1170, pp. 150-159 (1989).

Druy et al., *In-Situ Characterization of Resin Chemistry With Infrared Transmitting Optical Fibers and Infrared Spectroscopy*, Applied Spectroscopy, SPIE vol. 1437, pp. 66-74 (1991).

Young, et al. *FTIR Characterization of Advanced Materials*, 31st Nat. Sample Symp. (Apr., 1986).

Primary Examiner—Carolyn E. Fields
Attorney, Agent, or Firm—Fish & Richardson P.C.

[57] ABSTRACT

A radiation transmission optical fiber having a core and cladding for spectroscopic monitoring includes a transmission portion and a sensor portion; the transmission portion has a continuous core portion and a continuous cladding over the core portion; the sensor portion has the cladding removed from one side of the fiber and the core portion exposed from the same side leaving the continuous cladding intact over the opposite side of the core portion of the sensor.

28 Claims, 7 Drawing Sheets

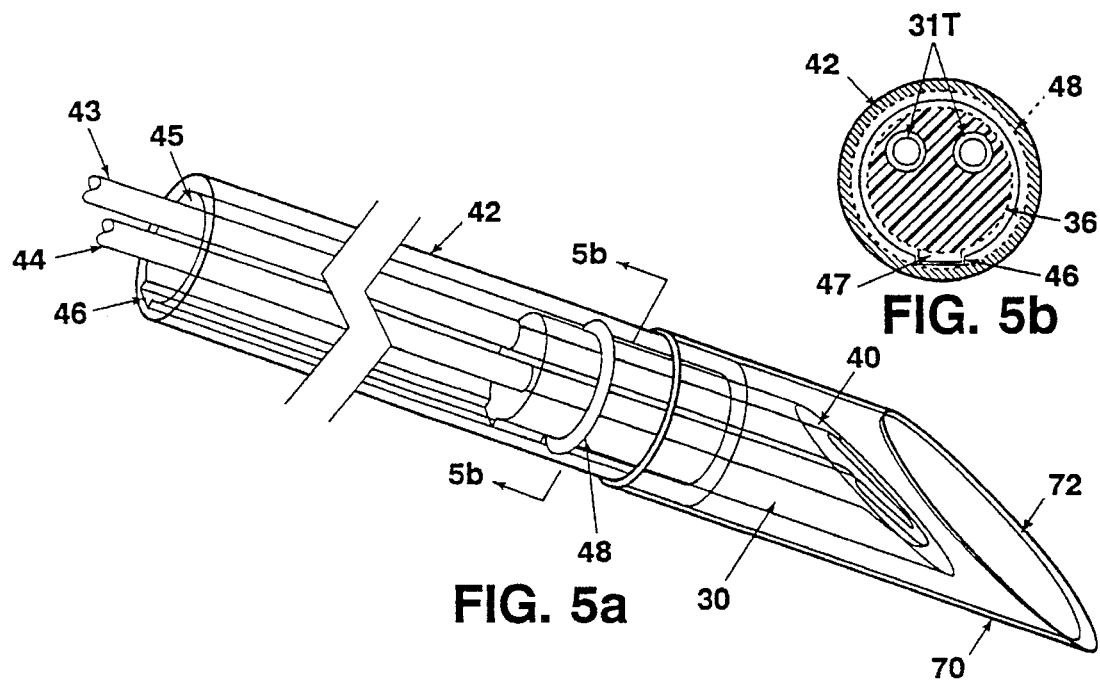
FIG. 5a
FIG. 5b
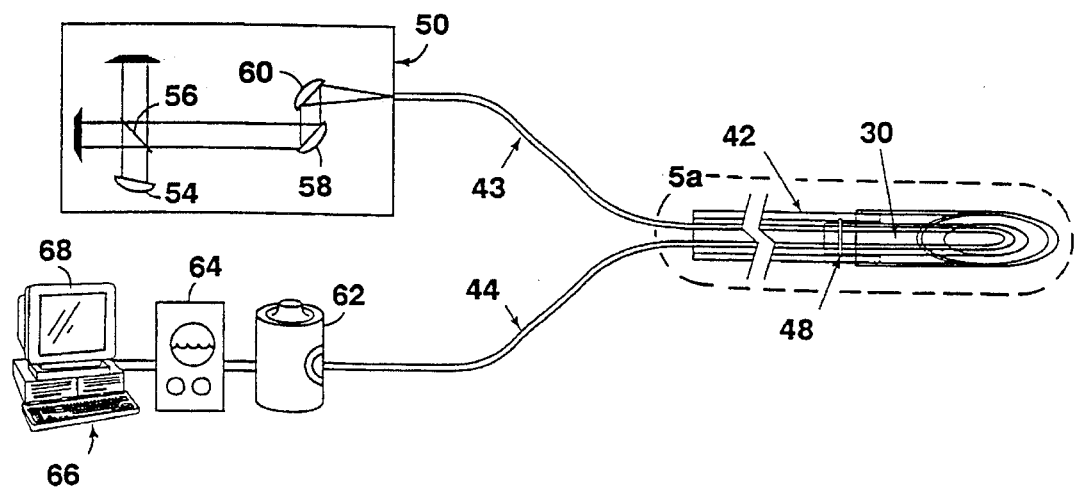
FIG. 5

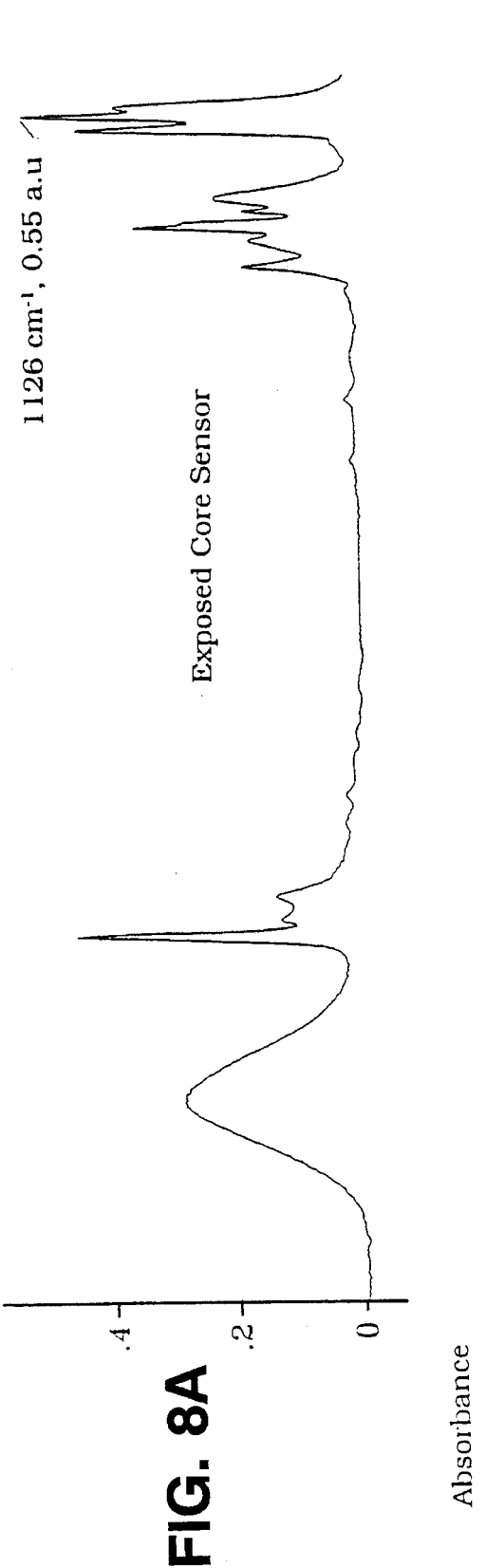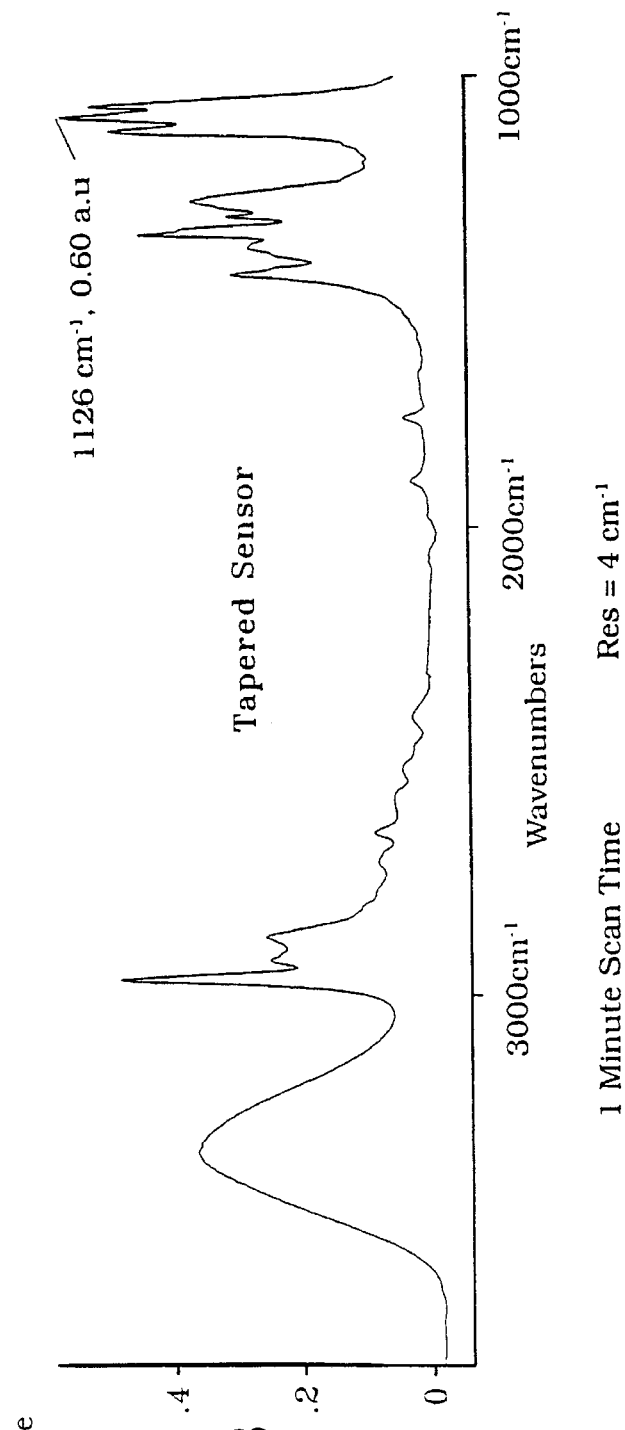
FIG. 8A
FIG. 8B

ATTENUATED TOTAL REFLECTANCE SENSING

BACKGROUND OF THE INVENTION

This invention relates to spectroscopic technology and more particularly to technology for analyzing material using optical fiber-attenuated total reflectance technology.

Spectroscopy is frequently employed in a qualitative and quantitative analysis of materials. Infrared radiation detection techniques are frequently advantageous over spectroscopic techniques using radiation of shorter wavelengths, such as a visible or ultraviolet light, as organic and biological materials have characteristic strong and relatively narrow unique identifying absorption peaks in the infrared region. Fourier transform infrared (FTIR) spectroscopic monitoring is useful in spectroscopy, as discussed, for example in Stevenson U.S. Pat. No. Re. 33,789, Bornstein et al. U.S. Pat. No. 5,070,243, Stevenson U.S. Pat. No. 5,239,176 and Cook U.S. Pat. No. 4,852,967. The material being analyzed or monitored may be gaseous, liquid or solid.

This invention relates to the use of an optical fiber as a multiple internal reflection (MIR) sensor and more particularly to the technology of using optical fibers as MIR sensors for performing both emission spectroscopy and absorption spectroscopic measurements of highly absorbing or highly scattering material, a technique sometimes referred to as attenuated total reflectance (ATR) or evanescent wave spectroscopy.

SUMMARY OF THE INVENTION

In accordance with one aspect of the invention, there is provided a radiation transmission fiber for spectroscopic monitoring that includes a transmission portion and a sensor portion. The transmission portion has a continuous core and continuous clad over one hundred percent of the transmission portion and between forty to sixty percent of the sensor portion. The remainder of the sensor portion has an exposed core surface (which is planar in particular embodiments but may be of other shape, such as cylindrical as appropriate), both the clad and core is either mechanically removed by grinding and polishing with suitable optical abrasive compounds or chemically removed by etching with a suitable etchant such as potassium hydroxide, zirconium oxychloride or hydrogen fluoride. The fiber may be as short as one centimeter and in a particular embodiment the sensor portion is about one centimeter long.

The sensor fiber core preferably is of a chalcogenide glass such as arsenic selenium tellurium, arsenic trisulfide, germanium selenium tellurium, arsenic germanium selenium; a heavy metal fluoride glass such as zirconium, barium, lanthanum, aluminum, sodium fluoride; fused silica or silicate glasses, or single crystal materials such as silver halides, thallium bromoiodiede and cesium halide or sapphire. Preferably, the core has an initial diameter before ablation of at least fifteen micrometers but less than one millimeter and a refractive index greater than 1.5. Preferably, the fiber includes structure for changing the mode structure of the light beam propagating within the fiber such as a sharp bend(s) and/or by conical transition portions such as tapers.

In a particular embodiment, the transmission portion has a chalcogenide glass core of about 750 micrometers diameter and a cladding layer of chalcogenide glass of about 100 or about 125 micrometers thickness; the sensor region core and cladding is ablated to approximately to the center of the core or to a total depth of about 500 micrometers over a length of approximately one centimeter. The optical fiber in the transmission portion has a numerical aperture of 0.5, the glass core has a glass transition temperature of 136° C., a thermal expansion coefficient of $23.6 \times 10^{-6}/°C$. and a refractive index at 10.6 micrometers wavelength of 2.81; while the glass cladding has a glass transition temperature of about 105° C. and a refractive index of about 2.18 at 10.6 micrometers wavelength.

When such a sensor is encapsulated or potted in a typical optical epoxy, the cladding and/or core glass in the sensor region can be precisely ablated to the desired depth using conventional optical grinding and polishing techniques. The optical epoxy provides a firm, tough support for the fiber and is ground and polished at the same rate as the glass. This provides a continuing firm support and mounting for the fiber that can be used for mounting and protecting the fragile sensor in a variety of different ATR probes. The evanescent wave propagating at the polished surface of the core glass is not absorbed by the epoxy as the cladding glass on the underside of the sensor region is the only part that is in intimate optical contact with the epoxy.

By combining this asymmetrically exposed core sensor with mode altering optical techniques such as simple bending in the shape of a U or using biconical tapers, qualitative and quantitative spectra measurements can be achieved that equal those obtained by the very best tapered core/clad sensors. One major difference is the ease of reproducible manufacture. Fibers can be precisely bent using simple fixtures and can be permanently secured in a variety of suitable optical cements. Sensor ablation can be precisely controlled using a variety of well known optical grinding and polishing equipment and techniques.

Permanent protective support for the sensor may be provided by potting it in a hard, tough and durable optical cement that does not interfere with the operation of the sensor. This is particularly true when the sensor is to be used for spectroscopically monitoring solids, abrasive powders, flowing viscous liquids, and high velocity gas streams.

In accordance with another aspect of the invention, there is provided a spectroscopy system that includes a source of radiation for generating a broad band beam of radiation, a detector, a spectrum analyzing apparatus, and an elongated radiation transmission fiber for disposition in an absorption medium comprising a transmission portion and a sensor portion, and coupling structure for optically coupling the transmission fiber to the source to transmit a beam of radiation through the fiber to the sensor portion and for coupling the absorbed beam back to the detector and the spectrum analyzing apparatus for analyzing the absorption medium in which said sensor portion is disposed. The fiber length may range from less than one centimeter to ten meters or more. The transmission and sensor portions are described previously.

BRIEF DESCRIPTION OF THE DRAWING

Other features and advantages of the invention will be seen as the following description of particular embodiments progresses, in conjunction with the drawings, in which:

FIG. 5 is a schematic diagram of a spectroscopic system employing the sensor of FIG. 4, FIG. 5A is an enlarged diagrammatic view, and FIG. 5B is a sectional view along the line 5B—5B of FIG. 5A;

FIG. 8A and FIG. 8B are graphs of absorbance spectra of 100 percent isopropanol obtained with a spectroscopic system of the type shown in FIG. 5 and with a fiber optic sensor in accordance with the invention depicted in FIG. 4 (FIG. 8A) and a tapered core/clad sensor of optimum design in accordance with Stevenson U.S. Pat. No. 5,239,176 (FIG. 8B).

DESCRIPTION OF PARTICULAR EMBODIMENTS

Figure 1:
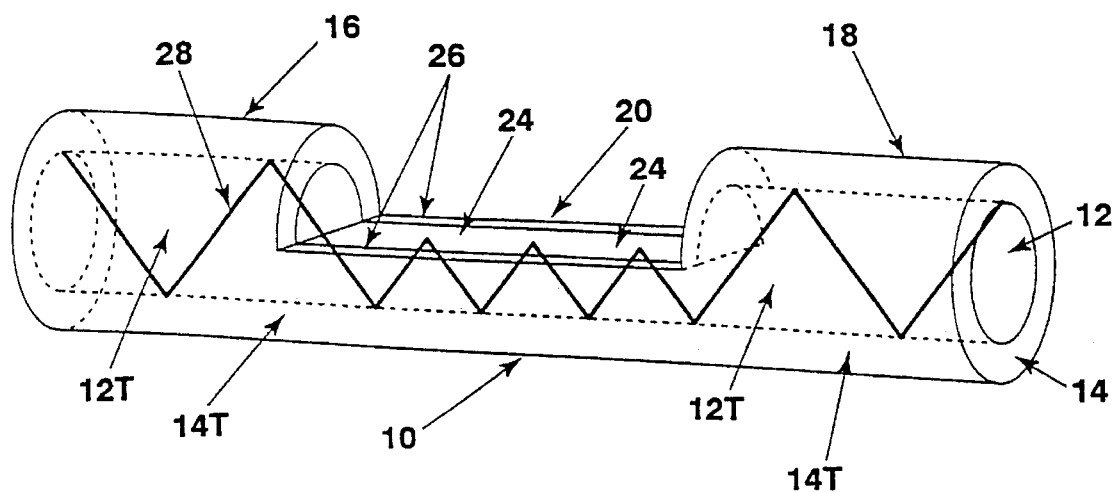
FIG. 1 is a diagrammatic view of an evanescent wave fiber optic sensor in accordance with the invention and FIG. 1A is a sectional view along the line 1A—1A of FIG. 1.
Figure 1A:
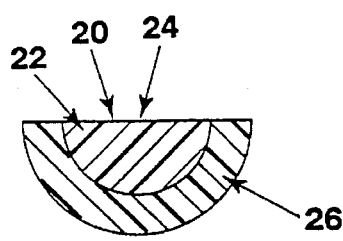

With reference to the diagrammatic views of FIGS. 1 and 1A, optical fiber 10 includes core portion 12 of arsenic, selenium, tellurium chalcogenide glass (AsSeTe) and cladding layer 14 of an arsenic sulfide (AsS) chalcogenide glass of lower refractive index. Fiber 10 has transmission portions 16, 18, transmission core portions 12T each having an outer diameter of approximately 750 micrometers and transmission clad portions 14T each having an outer diameter of approximately one millimeter. Sensor portion 20 has a length of about four centimeters with core portion 22 that is semicircular in shape and has relatively planar surface 24 that is approximately 750 micrometers wide, and semicircular cladding 26 that is approximately 125 micrometers thick. As indicated, a light ray 28 propagates at reflection angles within the numerical aperture of the fiber. More reflections occur per unit length in the sensor region 20 due to the reduced cross section of the core portion 22 in the sensor region 20.

Fiber 10 is processed by encapsulating the entire fiber in a suitable optical cement and then grinding and polishing the sensor region 20 with suitable optical abrasives until the core portion 22 and attached cladding portion 26 are approximately fifty percent removed or ablated and smooth planar sensor surface 24 is exposed.

Figure 2:
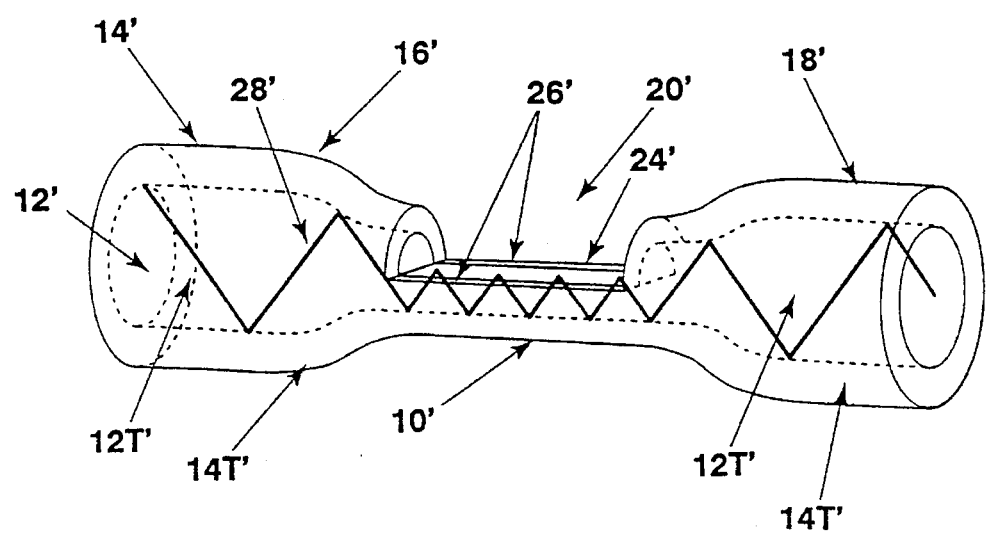
FIG. 2 is a diagrammatic view of another evanescent wave sensor in accordance with the invention.

FIG. 2 depicts a fiber 10' which contains tapers between the transmission portions 16' and 18' and the exposed core surface 24' of sensor portion 20'. The tapers are in accordance with teachings of Stevenson U.S. Pat. No. 5,239,176 and create more higher order modes in the sensor region 20' and then restore those modes to the normal propagating modes in the transmission region as shown by ray trace 28'; thus creating a more sensitive sensor.

Figure 3:
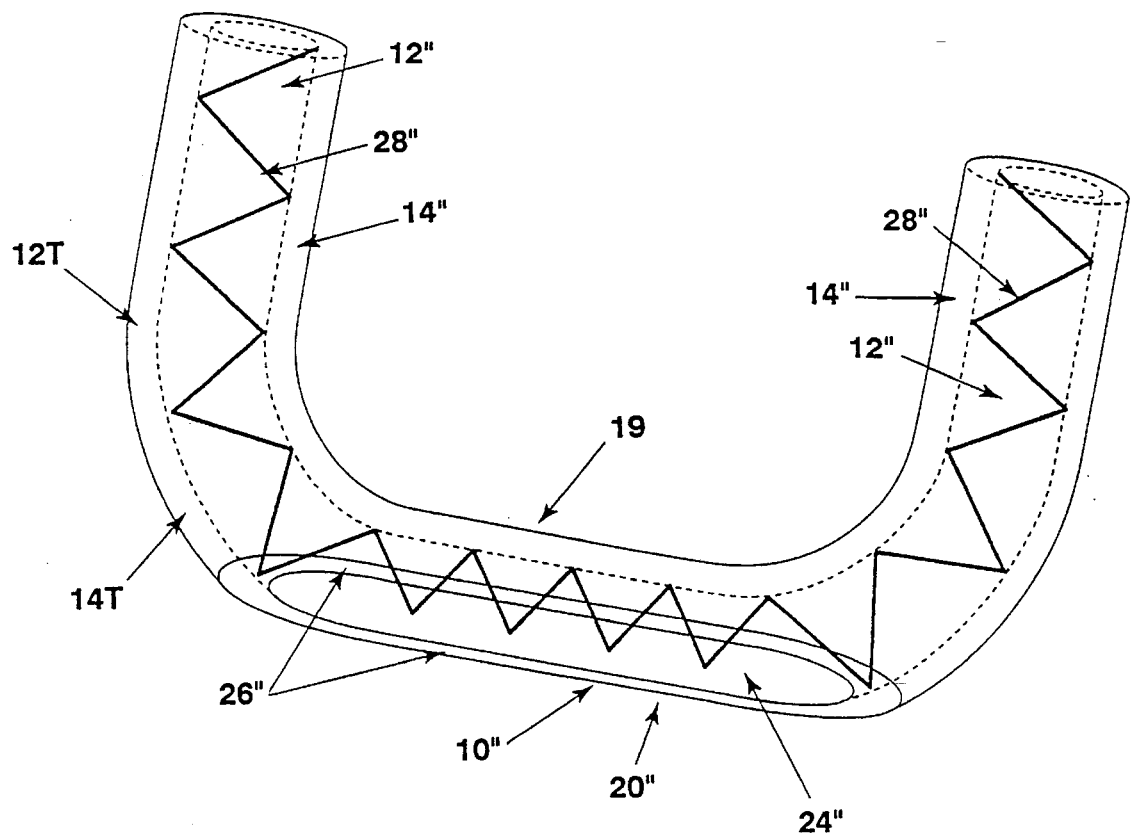
FIG. 3 is a diagrammatic view of an evanescent wave fiber optic sensor in accordance with the invention shaped in a U.

FIG. 3 depicts another sensor fiber 10" in accordance with the invention in the shape of a squared U with bight portion 19 in which sensor region 20" is disposed. The sensor region 20" is approximately two centimeters long and includes planar core surface 24". Asymmetric reordering of the mode structure to higher order modes is accomplished in the ninety degree bends in the transmission portions 16", 18".

Figure 4:
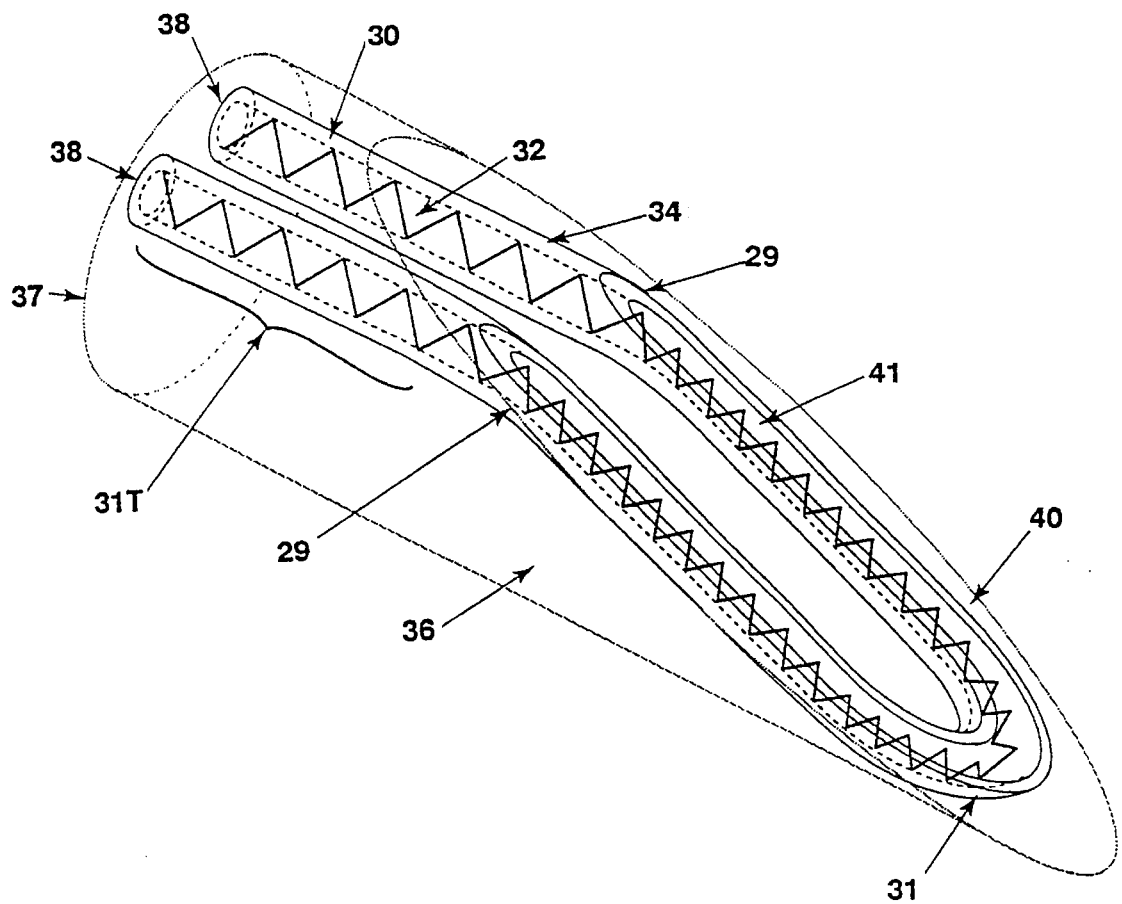
FIG. 4 is a diagrammatic view of still another evanescent wave fiber optic sensor shaped in a tight U bend with supplemental bends in the transmission portion just before and after the sensor region, and the entire fiber encapsulated in an optical cement.

FIG. 4 depicts another sensor fiber suitable for mounting in small diameter—approximately five millimeters—"needle probes" designed for making evanescent wave spectral measurements in confined spaces such as test tubes or small diameter cylinders. A tight U bend 31 of approximately two millimeters radius is combined with relatively low angle bends 29 to produce higher order modes in the sensor region 40 in a compact sensor.

With reference to FIG. 4, sensor 30 includes an optical fiber of type similar to the fibers of the sensors shown in FIGS. 1–3 and includes core portion 32 of about 750 micrometers outer diameter and cladding layer 34 of about 125 micrometers thickness. Fiber 31 is embedded in a suitable epoxy optical cement 36 such that terminal portions 38 at the end of transmission portions 31T are flush with the end surface 37 of epoxy 36. The fiber 30 is bent (29) twice, each at an angle of about 15° and again to form a tight U bend 31 of approximately two millimeters radius with the casing 36 having an outer diameter of about five millimeters. The epoxy casing support 36 is polished with suitable optical abrasives until the core portion 32 and attached cladding portion 34 are approximately fifty percent removed and a smooth planar sensor surface 40 is formed at an angle of about 15° to the axis of the cylindrical portion of casing 36. The tight U bend 31 of approximately two millimeters radius in the exposed surface 40, together with the relatively low angle bends 29 produce higher order modes in the sensor region 40 in a compact sensor that is about five millimeters in diameter and has a sensor surface 41 that is about one centimeter in length. A hard optically transparent coating of material such as magnesium fluoride may be applied to polished sensor surface 40 for use in contact measurement applications such as with abrasives, solids or human tissue.

Additional aspects of the sensor shown in FIG. 4 in combination with an FTIR analysis system are shown in FIG. 5. The sensor 30 is mounted in stainless steel probe support tube 42 in which coupling cables 44 are secured by suitable optical cement 45 and have coupling ends exposed within tube 42. Formed in tube 42 is keyway recess 46 and an annular recess that receives O-ring 48. Coupled to input transmission core clad fiber optic cable 44 is an FTIR spectrometer 50 of the Michelson interferometer type that includes infrared source 54, beam splitter 56 and focusing mirrors 58, 60. Coupled to core clad fiber optic output transmission cable 44 is an MCT (mercury cadmium teluride) detector 62, lock-in amplifier 64 and output processor 66 that includes display 68.

A sensor 30 of the type shown in FIG. 4 is inserted into housing 42 with axial and radial alignment by a key 47 that engages keyway 46 and the end surfaces 38 of the sensor fiber 31 are biased against the end surfaces of transmission cables 43, 44 by fluoroelastomer O-ring 48. A removable protective sheath 70 may be disposed over the protruding portion of sensor 30, the slanted end surface 72 being flush with sensor surface 40 for applications for monitoring solid material such as abrasive particles or human tissue, and protruding slightly where the material to be monitored is a liquid.

A sensor of the type in accordance with the invention depicted in FIG. 4 was connected to the analyzer apparatus depicted in FIG. 5. Measurements to determine sensor sensitivity, dynamic range, throughput and signal-to-noise ratios were performed as follows. The system was set for resolution of four wavenumbers (4 cm$^{-1}$), one minute scan time (52 scans), and a spectral range of from 4000 cm$^{-1}$ to 1000 cm$^{-1}$. Pure, anhydrous isopropanol was used as the test analyte.

With the sensor 30 connected, a single beam spectrum of the system in air was obtained. Then the sensor 30 was immersed in isopropanol and a second single beam spectrum of the system with the sensor 30 immersed in isopropanol was obtained. The second spectrum was ratioed against the first to produce an absorbance spectrum of isopropanol.

A tapered core/clad sensor of the type shown in U.S. Pat. No. 5,239,176 with appropriate transmission cables was then substituted for the FIG. 4 sensor and cables according to the invention and similar spectra were obtained under the same experimental conditions.

FIGS. 8A and 8B shows the comparative results. The ablated core sensor (FIG. 4) showed an absorbance peak height at 1126 cm$^{-1}$ (a major analytical peak for isopropanol) of 0.55 absorbance units whereas the tapered sensor shows an absorbance value of 0.6 absorbance units for the same peak. RMS noise was measured for both spectra in the region between 1810 cm$^{-1}$ and 1850 cm$^{-1}$. The total noise for the ablated core sensor of FIG. 4 was 0.00015 absorbance units resulting in a signal-to-noise ratio of 3,667 to 1. The total noise for the tapered sensor of the type shown in U.S. Pat. No. 5,239,176 was 0.00024 absorbance units between 1810 cm$^{-1}$ and 1850 cm$^{-1}$ resulting in signal-to-noise ratio of 2500 to 1. In overall performance the sensors are approximately equivalent.

Figure 6:
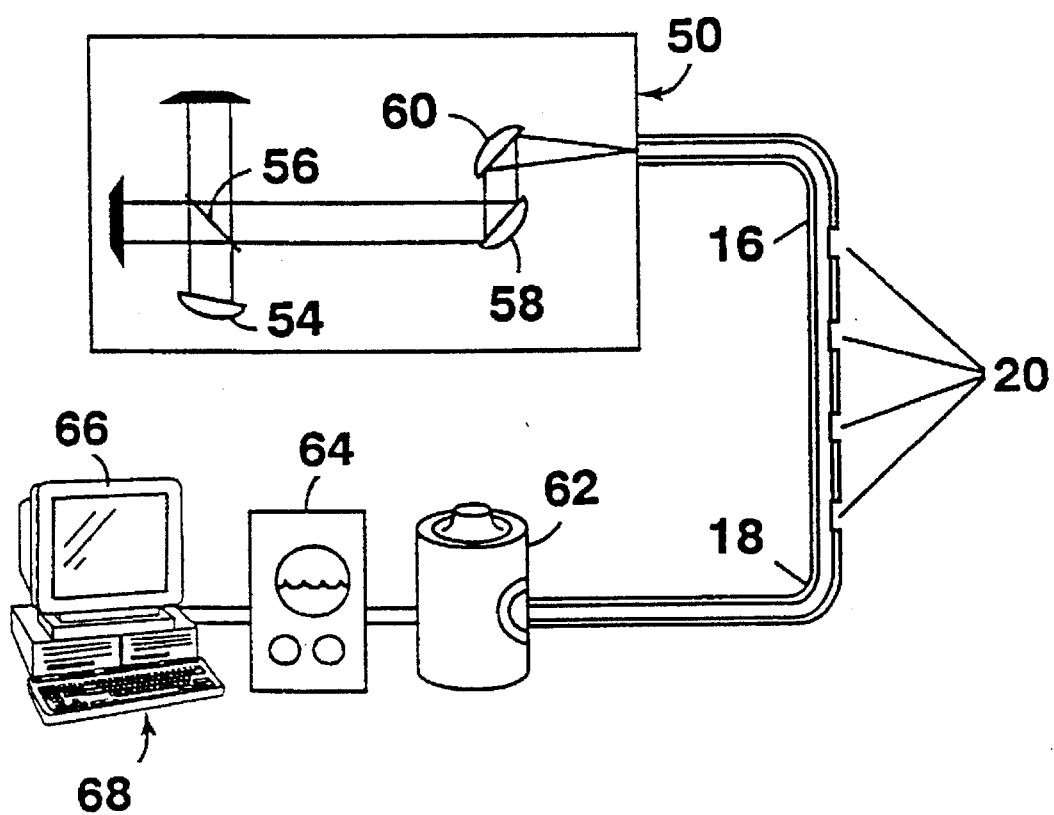
FIGS. 6 and 7 are schematic diagrams of variations of the system of FIG. 5.
Figure 7:
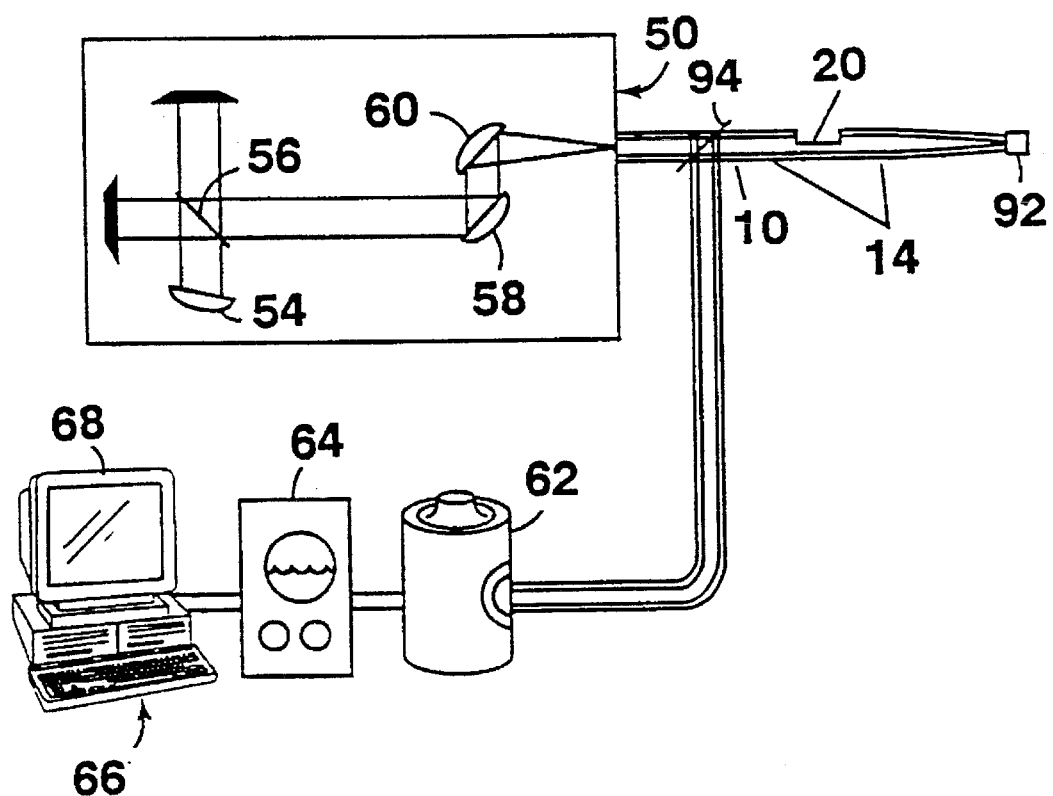

In another embodiment, shown in FIG. 7, the fiber 10 includes a single transmission portion 16 with retro-reflector 92 at the remote end of sensor portion 20 so that the transmitted beam as modified by absorbance at sensor 20 is reflected back through portion 16 to beam splitter 94; and in another embodiment, shown in FIG. 6, the fiber 10 has a number of sensors 20 created according to the invention along its length.

While particular embodiments of the invention have been shown and described, other embodiments will be apparent to those skilled in the art, and therefore, it is not intended that the invention be limited to the disclosed embodiments, or to details thereof, and departures may be made therefrom within the spirit and scope of the invention.

What is claimed is:

1. A radiation transmission fiber sensor for spectroscopic monitoring comprising an optical fiber with a transmission portion and a sensor portion, said transmission and sensor portions having a continuous core portion and cladding over said core portion throughout said transmission and sensor portions, said cladding in said sensor portion being of asymmetric configuration such that an unclad core surface portion in said sensor portion is provided for exposure to material to be spectroscopically monitored, said fiber being of U-shape configuration with two leg portions connected by a bight portion, and said exposed core surface portion extending through said bight portion into each said leg portion.

2. The sensor of claim 1 and further including encapsulating support structure surrounding said optical fiber with said unclad sensor surface portion exposed at a surface of said support structure.

3. The sensor of claim 1 wherein said cladding in said transmission portion has a thickness sufficient to contain the evanescent field at wavelengths of analytical interest.

4. The sensor of claim 1 wherein said core portion is selected from the group consisting of chalcogenide glass, heavy metal fluoride glass, oxide glass, and crystalline materials.

5. The sensor of claim 1 wherein said sensor core portion has a diameter in the range of 15–1,000 micrometers and a refractive index greater than 1.5.

6. The sensor of claim 1 wherein said transmission portion has a chalcogenide glass core of about 750 micrometers diameter and a cladding layer of chalcogenide glass of about 100 micrometers thickness; and the exposed core surface in said sensor region has a length of at least about one centimeter and a width of less than one centimeter.

7. The sensor of claim 1 wherein said exposed core surface is planar and has a width of at least about one third the diameter of said core portion.

8. The system of claim 1 wherein said fiber further includes low angle bends in said leg portions spaced from said bight portion.

9. The system of claim 8 wherein the angle of said low angle bends is about 15°.

10. The sensor of claim 9 wherein said cladding in said transmission portion has a thickness sufficient to contain the evanescent field at wavelengths of analytical interest, and further including encapsulating support structure surrounding said optical fiber with said unclad sensor surface portion exposed at a surface of said support structure.

11. The sensor of claim 1 and further including sensor housing structure and structure for releasably retaining said sensor in said housing structure.

12. The sensor of claim 11 wherein said core is selected from the group consisting of chalcogenide glass, heavy metal fluoride glass, oxide glass, and crystalline materials.

13. The sensor of claim 12 wherein said sensor core portion has a diameter in the range of 15–1,000 micrometers and a refractive index greater than 1.5.

14. The sensor of claim 13 wherein said exposed core surface portion is planar and has a width of at least about one third the diameter of said core portion.

15. The sensor of claim 14 wherein said transmission portion has a chalcogenide glass core of about 750 micrometers diameter and a cladding layer of chalcogenide glass of about 100 micrometers thickness; and the exposed core surface in said sensor region has a length of at least about one centimeter and a width of less than one centimeter.

16. A spectroscopy system comprising a source of radiation for generating a beam of radiation, spectrum analyzing apparatus, a sensor including an elongated radiation transmission fiber for disposition in a material of interest comprising a transmission portion and a sensor portion, said transmission and sensor portions having a continuous core portion and cladding over said core portion throughout said transmission and sensor portions, said cladding in said sensor portion being of asymmetric configuration such that an unclad core surface portion in said sensor portion is provided for exposure to material to be spectroscopically monitored, and coupling structure for coupling said transmission fiber to said source to transmit a beam of infrared radiation through said fiber to said sensor portion and for coupling said fiber to said analyzing apparatus for analyzing the absorption medium in which said sensor portion is disposed.

17. The system of claim 16 wherein said source is of the Michelson interferometer type and generates said beam of infrared radiation.

18. The system of claim 16 wherein said analyzing apparatus is of the Fourier transform type.

19. The system of claim 16 and further including encapsulating support structure surrounding said optical fiber with said sensor surface exposed at a surface of said support structure.

20. The system of claim 16 wherein said cladding in said transmission portion has a thickness sufficient to contain the evanescent field at wavelengths of analytical interest.

21. The system of claim 16 wherein said core portion is selected from the group consisting of chalcogenide glass, heavy metal fluoride glass, oxide glass, and crystalline materials.

22. The system of claim 16 wherein said sensor core portion has a diameter in the range of 15–1,000 micrometers and a refractive index greater than 1.5.

23. The system of claim 16 wherein said transmission portion has a chalcogenide glass core of about 750 micrometers diameter and a cladding layer of chalcogenide glass of about 100 micrometers thickness; and the exposed core surface in said sensor region has a length of at least about one centimeter and a width of less than one centimeter.

24. The system of claim 16 wherein said exposed surface is planar and has a width of at least about one third the diameter of said core portion.

25. The system of claim 24 wherein said fiber is formed in U-shape with a bight portion and said exposed core surface extends into said bight portion.

26. The system of claim 16 wherein said fiber is formed in U-shape with a bight portion and said exposed core surface extends into said bight portion.

27. The system of claim 26 wherein said source is of the Michelson interferometer type and generates a beam of infrared radiation; and said analyzing apparatus is of the Fourier transform type.

28. The sensor of claim 27 and further including sensor housing structure and structure for releasably retaining said sensor in said housing structure.

* * * * *